(12) United States Patent
Kubota (10) Patent No.: US 10,940,104 B2
(45) Date of Patent: Mar. 9, 2021

(54) OIL IN WATER TYPE SOLID COSMETIC

(71) Applicant: SHISEIDO COMPANY, LTD., Tokyo (JP)

(72) Inventor: Shun Kubota, Kanagawa (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/095,223

(22) PCT Filed: Apr. 27, 2017

(86) PCT No.: PCT/JP2017/016871
§ 371 (c)(1),
(2) Date: Oct. 19, 2018

(87) PCT Pub. No.: WO2017/188420
PCT Pub. Date: Nov. 2, 2017

(65) Prior Publication Data
US 2019/0133916 A1 May 9, 2019

(30) Foreign Application Priority Data

Apr. 28, 2016 (JP) .............................. JP2016-090763

(51) Int. Cl.
*A61K 8/86* (2006.01)
*A61K 8/06* (2006.01)
(Continued)

(52) U.S. Cl.
CPC .................. *A61K 8/86* (2013.01); *A61K 8/02* (2013.01); *A61K 8/0216* (2013.01); *A61K 8/06* (2013.01);
(Continued)

(58) Field of Classification Search
None
See application file for complete search history.

(56) References Cited

U.S. PATENT DOCUMENTS 4,801,445 A  1/1989 Fukui
4,818,614 A  4/1989 Fukui
(Continued)

FOREIGN PATENT DOCUMENTS

EP  2565233 A1  3/2013
JP  H0154380 B2  11/1989
(Continued)

OTHER PUBLICATIONS

JP2007/291026A—Google English Translation (Year: 2007).*

(Continued)

*Primary Examiner* — Kyung S Chang
(74) *Attorney, Agent, or Firm* — Rankin, Hill & Clark LLP (57) ABSTRACT

To provide an oil in water type solid cosmetic composition which can be solidified into a stable solid shape, has a desired sensation of elasticity, has favorable take up properties when taken up with a finger, and imparts a superior sensation of freshness when utilized, as an oil in water type preparation. An oil in water type solid cosmetic includes: (a) 0.1 to 5% by mass of a hydrophobically modified polyether urethane; (b) 0.01 to 5% by mass of a hydrophilic plate shaped powder; (c) a hydrophobic powder; (d) an oil component; and (e) water.

7 Claims, 3 Drawing Sheets

(51) Int. Cl.
*A61K 8/87* (2006.01)
*A61K 8/02* (2006.01)
*A61Q 1/10* (2006.01)
*A61Q 1/00* (2006.01)
*A61Q 1/02* (2006.01)
*A61Q 19/00* (2006.01)

(52) U.S. Cl.
CPC ............... *A61K 8/062* (2013.01); *A61K 8/87* (2013.01); *A61Q 1/00* (2013.01); *A61Q 1/02* (2013.01); *A61Q 1/10* (2013.01); *A61Q 19/00* (2013.01)

(56) References Cited

U.S. PATENT DOCUMENTS

| | | | |
|---|---|---|---|
| 4,882,225 A | 11/1989 | Fukui | |
| 6,440,431 B1 | 8/2002 | Yoshida | |
| 2013/0156831 A1 | 6/2013 | Matsuo | |
| 2014/0251202 A1* | 9/2014 | McGuire | A61K 8/26 117/71 |
| 2015/0005396 A1* | 1/2015 | Watanabe | A61Q 19/00 514/788 |
| 2017/0172893 A1 | 6/2017 | Igarashi | |

FOREIGN PATENT DOCUMENTS

| | | |
|---|---|---|
| JP | H0154381 B2 | 11/1989 |
| JP | 2000239120 A | 9/2000 |
| JP | 2003095862 A | 4/2003 |
| JP | 2007291026 A | 11/2007 |
| JP | 2011020966 A | 2/2011 |
| JP | 2011231061 A | 11/2011 |
| JP | 2013-82663 A | 5/2013 |
| JP | 2013189428 A | 9/2013 |
| JP | 2014198672 A | 10/2014 |
| JP | 2015199708 A | 11/2015 |
| WO | 2008018541 A1 | 2/2008 |
| WO | 2015146948 A1 | 10/2015 |

OTHER PUBLICATIONS

International Search Report dated Aug. 8, 2017 filed in PCT/JP2017/016871.
International Search Opinion dated Aug. 8, 2017 filed in PCT/JP2017/016871; partial translation.
Extended European Search Report (EESR) dated Nov. 12, 2019 issued in the corresponding European patent application No. 17789701.04.
European Office Action dated Jun. 9, 2020 issued in the corresponding European Patent Application No. 17789701.4.

* cited by examiner

MARK LEFT BY SAMPLE BREAKING AND BEING CHIPPED

MEASUREMENT NEEDLE

BROKEN SAMPLE

STATE OF SOLID SAMPLE A AFTER MEASUREMENT

DOWNWARDLY RECESSED DEFORMED MEASUREMENT LOCATION

STATE OF SOLID SAMPLE B AFTER MEASUREMENT

TRACE OF MEASUREMENT AT PORTION OF MEASUREMENT NEEDL

RESTORED ABOVE DEPTH OF MEASUREMENT (PENETRATION: 1 mm)

STATE OF SOLID SAMPLE C AFTER MEASUREMENT

OIL IN WATER TYPE SOLID COSMETIC

CROSS REFERENCE TO RELATED APPLICATIONS

The present application is a National Phase Entry of PCT International Application No. PCT/JP2017/016871 filed on Apr. 27, 2017, which claims priority under 35 U.S.C. § 119(a) to Japanese Patent Application No. 2016-090763 filed on Apr. 28, 2016. Each of the above applications is hereby expressly incorporated by reference, in its entirety, into the present application.

BACKGROUND

Technical Field

The present disclosure is related to an oil in water type solid cosmetic, and more specifically to an oil in water type solid cosmetic having elasticity, favorable applicability, and a superior sensation of freshness.

Background Art

In recent years, solid cosmetics having a tactile sensation of elasticity have been attracting attention and are gaining popularity. For example, blush, eye shadow, etc., to which elasticity is imparted by blending an elastomer powder in an oily component, are known. However, conventional solid cosmetics having such elasticity are all of the oil based type. Therefore, there is an oily sensation as a feeling of use, a lack of a sensation of freshness, and also a problem from a functional viewpoint that the cosmetic is not long lasting.

On the other hand, oil in water type cosmetics which are obtained by solidifying an aqueous system with agar, gelatin, etc., have been attracting attention as having a sensation of freshness and a high refreshing feeling. However, such cosmetics which are obtained by solidifying an aqueous system with agar, etc. are mostly in the form of a gel. If a cosmetic in the form of a gel is to be solidified further, it will become difficult to be manually applied, and also a desired sensation of elasticity will not be obtained. Japanese Unexamined Patent Publication No. 2003-95862 discloses an oil in water type solid cosmetic composition containing agar and/or gelatin, polyethylene glycol having a specific molecular weight, an oil agent, and water. However, the cosmetic of Japanese Unexamined Patent Publication No. 2003-95862 does not have a desired sensation of elasticity.

Meanwhile, skin cosmetic compositions containing associative thickening agents such as hydrophobically modified polyurethane have a unique sensation of elasticity, and therefore are utilized as beautifying solutions etc. For example, International Patent Publication No. WO 2008/018541, Japanese Unexamined Patent Publication No. 2011-20966 and Japanese Unexamined Patent Publication No. 2011-231061 disclose oil in water type emulsified cosmetics using hydrophobically modified polyether urethane as a thickening agent. However, all of these cosmetics are liquid or in the form of a gel, and it is difficult to solidify these cosmetics while maintaining elasticity. If an attempt is made to solidify an emulsified cosmetic that contains a hydrophobic polyether urethane with a powder or a gelling agent, there is a problem that the cosmetic will solidify and cleavage properties will be lost to a degree that would cause it to become difficult to take up the cosmetic with a finger or an applicator, etc.

In aqueous cosmetics, development of a water based solid cosmetic which can be molded into a solid (balm) form in a state that can be favorably taken up by a finger and imparts a sensation of elasticity when touched has been strongly desired.

SUMMARY

The present disclosure provides an oil in water type solid cosmetic, which can be solidified in an aqueous system while maintaining elasticity, has a desired sensation of elasticity as a feeling of use, can be favorably taken up by a finger, exhibits superior freshness as a feeling of use, and is a long lasting cosmetic as a functional aspect.

As a result of extensive research in order to achieve such an oil in water type solid cosmetic, the inventors discovered that by blending a hydrophilic plate shaped powder in addition to a hydrophobic powder in an oil in water type preparation that includes a hydrophobically modified polyether urethane as an associative thickening agent, such a preparation can be hardened to a solid state while maintaining elasticity, have a soft elastic sensation, can be taken up easily with a finger, and further imparts a feeling of freshness when applied to the skin to produce and obtain a water type solid cosmetic, and thereby developed the present disclosure.

The oil in water type solid cosmetic of the present disclosure is characterized by comprising:
(a) 0.1 to 5% by mass of a hydrophobically modified polyether urethane represented by Formula (I) below;
(b) 0.01 to 5% by mass of a hydrophilic plate shaped powder;
(c) a hydrophobic powder;
(d) an oil component; and
(e) water;

Formula (I):

wherein:
$R_1$, $R_2$ and $R_4$ each independently represent a hydrocarbon group having 2 to 4 carbon atoms;
$R_3$ represents a hydrocarbon group having 1 to 10 carbon atoms which may have a urethane bond;
$R_5$ is a hydrocarbon group having 8 to 36 carbon atoms;
m is a number 2 or greater;
h is a number 1 or greater;
k is a number within a range from 1 to 500; and
n is a number within a range from 1 to 200. The plate shaped hydrophilic powder which is contained in the aqueous phase (outer layer) having favorable cleavage properties "connects" an oil phase (inner layer) that contains the hydrophobic powder via the hydrophobically modified polyether urethane. Thereby, water separation can be prevented and a solid state can be stably maintained while maintaining elasticity. Further, because the bond can be broken by a slight force when being taken up by a hand, the cosmetic can be favorably taken up with a finger, has favorably spreading properties on the skin, and can realize a sensation of freshness.

It is preferable for the hydrophilic plate shaped powder to have an average aspect ratio within a range from 10 to 100, more preferably an average aspect ratio within a range from 20 to 100, and still more preferably an average aspect ratio within a range from 40 to 100. By employing a hydrophilic plate shaped powder having a higher aspect ratio, breaking of the "connection" structure is facilitated when taken up by a hand, which facilitates taking up by a finger, as well as providing a sense of freshness. If the average aspect ratio is less than 10, there is a tendency for the ease with which the cosmetic is taken up by a finger to deteriorate, and if the average aspect ratio is greater than 100, there may be cases in which stability deteriorates.

The hydrophobically modified polyether urethane is not limited, but from the viewpoint of elasticity, a (PEG-240/decyltetradeceth-20/HDI) copolymer may be favorably employed in the present disclosure.

The oil in water type solid cosmetic composition of the present disclosure is not limited, but may be molded into a solid (balm) form, may be employed as a makeup cosmetic, for example.

The oil in water type solid cosmetic composition of the present disclosure has a unique tactile sensation having elasticity, is capable of being taken up by a finger easily, and imparts a fresh feeling of use with favorable spreading properties.

DETAILED DESCRIPTION OF THE EMBODIMENTS

<(a) Hydrophobically Modified Polyether Urethane>

The hydrophobically modified polyether urethane which is employed as component (a) in the present disclosure is represented by Formula (I) below:

This copolymer is an associative thickening agent. The associative thickening agent is a copolymer having a hydrophilic base portion as a skeleton, and hydrophobic portions at the terminals thereof. The hydrophobic portions of the copolymer are associated with each other in an aqueous medium, the hydrophilic portion assumes a loop form and a bridge form, and exhibits an increased viscous function.

In Formula (I) above, each of $R_1$, $R_2$ and $R_4$ independently represent a hydrocarbon group having 2 to 4 carbon atoms. Preferably, each of $R_1$, $R_2$ and $R_4$ is an alkylene group having 2 to 4 carbon atoms.

$R_3$ represents a hydrocarbon group having 1 to 10 carbon atoms which may have a urethane bond, and is preferably an alkylene group having 1 to 10 carbon atoms.

$R_5$ represents a hydrocarbon group having 8 to 36 carbon atoms, preferably 12 to 24 carbon atoms, and more preferably represents a linear, branched or secondary alkyl group having 12 to 24 carbon atoms.

m is a number 2 or greater. It is preferable for m to be 2.

h is a number 1 or greater. It is preferable for h to be 1.

k is a number within a range from 1 to 500. It is preferable for k to be a number within a range from 100 to 300.

n is a number within a range from 1 to 200. It is preferable for n to be a number within a range from 10 to 100.

A favorable method for obtaining the hydrophobically modified polyether urethane represented by Formula (I) above is reacting one type or two or more types of polyether polyols represented by $R_1-[(O-R_2)_k-OH]_m$ (wherein $R_1$, $R_2$, k, m are as defined above), one type or two or more types of polyisocyanates represented by $R_3-(NCO)_{h+1}$ (wherein $R_3$ and h are as defined above), and one type or two or more types of polyether monoalcohols represented by $HO-(R_4-O)_n-R_5$ (where $R_4$, $R_5$, and n are as defined above), for example. In this case, $R_1$ through $R_5$ in Formula (I) are determined by the compounds represented by $R_1-[(O-R_2)_k-OH]_m$ and $R_3(NCO)_h$, and $HO-(R_4-O)_n-R_5$ which are employed. The charging ratios of the above three compounds is not particularly limited. However, it is preferable for the ratio of hydroxyl groups derived from polyether polyol and polyether monoalcohol with respect to isocyanate groups derived from polyisocyanate to be NCO/OH=0.8:1 to 1.4 to 1. Details of the method for producing the hydrophobically modified polyether urethane represented by Formula (I) are disclosed in, for example, International Patent Publication No. WO 2008/018541, Japanese Unexamined Patent Publication No. 2011-20966, etc.

Alternatively, commercially available products may be employed as the hydrophobically modified polyether urethane. Examples of such commercially available products include Adekanol UH 140 S, Adekanol UH-420, Adekanol UH-438, Adekanol UH-750 and Adekanol GT-700 (by ADEKA); Serad-FX1100, Serad-FX1010, and Serad-FX1035 (by HULS); Rheolate 205, Rheolate 208, Rheolate 204, Rheolate 225, Rheolate 278, and Rheolate 244 (by Rheox), DW 1206F, DW 1206J, and DW 1206G (by Rohm & Haas); Dapral-T212 (by Akzo); Borchigel-LW44 and Borchigel-L75N (by Borchers); etc.

A (PEG-240/decyltetradeceth-20/HDI) copolymer (the copolymer represented by Formula (I) above, wherein $R_1$, $R_2$ and $R_4$ respectively are an ethylene group, $R_3$ is a hexamethylene group, $R_5$ is a 2-dodecyldodecyl group, h=1, m=2, k=120, and n=20) is particularly preferable as component (a). This copolymer is commercially available from ADEKA under the product name "Adekanol GT-700".

The content of component (a) is 0.1 to 5% by mass and preferably 0.2 to 3% by mass with respect to the total amount of the cosmetic. If the content of component (a) is less than 0.1% by mass, sufficient elasticity cannot be realized. On the other hand, if the content of component (a) is greater than 5% by mass, there is a tendency for the viscosity to become excessively high, resulting in a decrease in production efficiency or causing difficulty in suppressing stickiness, which is not preferable.

<(b) Hydrophilic Plate Shaped Powder>

In the present disclosure, the hydrophilic plate shaped powder (component (b)) functions as a "connection" that connects an oil phase (inner layer) containing the hydrophobic powder which is blended in an external phase (aqueous phase). By "connecting" with a plate shaped hydrophilic powder having good cleavage properties, the cosmetic can be stably maintained in a solid shape that can be molded into a container while maintaining elasticity. Further, taking up by a finger is facilitated because a slight force can break the connection when taking up with a hand. In addition, spreading properties on the skin are favorable, and a sensation of freshness can be realized. The hydrophilic plate shaped powder used in the present disclosure is not particularly limited as long as it is a hydrophilic plate shaped (flake form) powder which is generally utilized in cosmetics. A plate shaped powder is distinguished from a spherical powder by having an aspect ratio (average particle diameter/average thickness) of greater than 1, and for example, at least 5 or greater. Although the aspect ratio of the plate shaped powder in the present disclosure is not particularly limited as long as it is in the shape of a plate (flake form), it is preferable for the hydrophilic plate shaped powder to have an average aspect ratio within a range from 10 to 100, more preferably an average aspect ratio within a range from 20 of 100 and still more preferably an average aspect ratio within a range from 40 to 100. If the average aspect ratio is less than 10, there is a tendency for the ease with which the cosmetic is taken up by a finger to deteriorate, and if the average aspect ratio is greater than 100, there may be cases in which stability deteriorates. In addition, although the particle size is not particularly limited, a plate shaped powder having an average particle size within a range from 0.1 to 100 μm may be favorably employed from the viewpoint of ease of taking up with a finger.

Specific examples of plate shaped powders include mica, sericite, talc, kaolin, alumina, barium sulfate, boron nitride, N-acylated lysine, synthetic phlogopite, synthetic mica, synthetic talc, zinc oxide, silica, fish scale foil, bismuth oxychloride, etc. One type or two or more types from among these may be selected and employed. The hydrophilic plate shaped powder in the present disclosure may be that which has undergone surface treatment or that which has not undergone surface treatment. For example, synthetic mica which are commercially available under the product names of synthetic mica PDM-5L, PDM-7L, PDM-9L, PDM-10L, PDM-20L, ST (HS), and Helios by Topy Industries, Fit Powder FK-3005, FK-5005, Mica Powder Y-1800, Y-2300, Y-2400, Y-3000, Mica Powder SA-310, SA-350, Mica Powder NCC-322, NCF-322, NCR-300, and Mica Powder FA-450 by Yamaguchi Mica, Sericite FSE sold by Sanshin Mining Industries, etc. may be favorably employed.

It is preferable for the content of the hydrophilic plate shaped powder in the oil in water type solid cosmetic of the present disclosure to be 0.01 to 5% by mass, preferably 0.01 to 2.5% by mass, and more preferably 0.05 to 1% by mass. If the content of the hydrophilic plate shaped powder is less than 0.01% by mass, water separation becomes likely to occur and there are cases in which the cosmetic will become unstable. If the content is greater than 5% by mass, a sensation of roughness will be felt due to the powder, which is not preferable.

<(C) Hydrophobic Powder>

The hydrophobic powder which is employed as component (c) in the present disclosure includes not only powders which are hydrophobic itself but also hydrophobic powders which are hydrophilic powder and the like but become hydrophobized powders by subjecting the powder surfaces to hydrophobic treatment. Hydrophobic powders have strong water repellent properties, are resistant to water and sweat, and impart long lasting effects to makeup, and therefore exhibit superior sustainability of cosmetic effects. In the present disclosure, the connection formed by the hydrophilic plate shaped powder may be broken due to the load when the cosmetic is applied to the skin, the outer layer (aqueous phase) softens and spreads to impart a sensation of freshness, and the hydrophobic powder of the inner layer (oil phase) adheres favorably to the skin may impart a cosmetic effect.

Specific examples of the hydrophobic powder include organic powders such as polyamide resin powder (nylon powder), polyethylene powder, polymethyl methacrylate powder, polystyrene powder, styrene and acrylic acid copolymer resin powder, benzoguanamine resin powder, polytetrafluoride ethylene powder; and cellulose powder, as well as silicone powders such as trimethyl silsesquioxane powder, etc.

Examples of powder components of the hydrophobized powder include inorganic powders such as talc, kaolin, mica, sericite, muscovite, phlogopite, synthetic mica, lepidolite, biotite, lithia mica, permiculite, magnesium carbonate, calcium carbonate, aluminum silicate, barium silicate, calcium silicate, magnesium silicate, strontium silicate, metal tungstate salt, magnesium, silica, zeolite, barium sulfate, sintered calcium sulfate (burnt plaster), calcium phosphate, fluoroapatite, hydroxyapatite, ceramic powder, metal soap (zinc myristate, calcium palmitate, aluminum stearate, etc.) and boron nitride; inorganic white pigments such as titanium dioxide and zinc oxide; inorganic red series pigments such as iron oxide (red iron oxide) and iron titanate; inorganic brown series pigments such as γ-iron oxide, inorganic yellow series pigments such as yellow iron oxide and ocher; inorganic black series pigments such as black iron oxide, carbon black, and low order titanium dioxide; inorganic purple series pigments such as mango violet and valto violet; inorganic green series pigments such as chromium oxide, chromium hydroxide, and cobalt titanate; inorganic blue series pigments such as ultramarine and iron blue; pearl pigments such as mica titanium, iron oxide coated mica titanium, carmine coated mica titanium, carmine.iron blue coated mica titanium, iron oxide/carmine treated mica titanium, iron blue treated mica titanium, iron oxide/iron blue treated mica titanium, chromium oxide coated treated mica titanium, black titanium oxide treated mica titanium, acrylic resin coated aluminum powder, titanium oxide coated mica, titanium oxide coated oxy bismuth chloride, titanium oxide coated talc, colored titanium oxide coated mica, oxy bismuth chloride, and argentine; and metal powder pigments such as aluminum powder and copper powder. The present disclosure employs hydrophobized powders which are obtained by subjecting these powder components to hydrophobic treatment.

Any hydrophobic treatment method may be employed as long as it is a method which is capable of imparting water repellent properties, and there is no particular limitation on the method. For example, a standard surface treatment method such as the vapor phase method, the liquid phase method, the autoclave method, and the mechanochemical method may be employed.

For example, in the case that a hydrophobic treatment is performed by adding a hydrophobizing agent to a raw material powder, the hydrophobizing agent may be added after being diluted in an appropriate solvent (dichloromethane, chloroform, hexane, ethanol, xylene, volatile silicone, etc.), or may be added directly. A ball mill, a ho jar site ball mill, a vibrating ball mill, an attritor, a pot mill, a rod mill, a pan mill, a homomixer, a homodisper, a Henschel mixer, a Nauta mixer or the like may be employed to mix and stir the powder and the hydrophobizing agent. As alternatives to this method, a method that utilizes the activity of the powder surface to polymerize cyclic organosiloxane on the powder surface at a low temperature of 100° C. or less by a gas phase reaction (Japanese Examined Patent Publication No. H01-54380), a method in which a pendant group such as glycerol monoallyl ether is added to the Si—H moiety of a silicone polymer on the surface of a powder after administering the aforementioned method (Japanese Examined Patent Publication No. H01-54381) and the like may also be employed.

The hydrophobizing agent is not particularly restricted but is preferably a low viscosity to high viscosity oily polysiloxane treated powder such as a fatty acid dextrin treated powder, a trimethylsiloxysilicic acid-treated powder, a fluorine modified trimethylsiloxysilicic acid treated powder, a methylphenylsiloxysilicic acid treated powder, a fluorine modified methylphenylsiloxysilicic acid treated powder, dimethyl polysiloxane, diphenyl polysiloxane, and methyl phenyl polysiloxane; an organic silyl compound such as a gum polysiloxane treated powder, a methyl hydrogen polysiloxane treated powder, a fluorine modified methyl hydrogen polysiloxane treated powder, methyltrichlorosilane, methyltrialkoxysilane, hexamethyldisilane, dimethyldichlorosilane, dimethyl dialkoxysilane, trimethylchlorosilane, trimethylalkoxysilane or a powder treated with a fluorine substitution product thereof; an organic modified silane such as ethyltrichlorosilane, ethyltrialkoxysilane, propyltrichlorosilane, propyltrialkoxysilane, hexyltrichlorosilane, hexyltrialkoxysilane, long chain alkyltrichlorosilane, and long chain alkyltriethoxysilane or a powder treated with a fluorine substitution product thereof; an amino-modified polysiloxane treated powder, a fluorine modified polysiloxane treated powder, a fluorinated alkylphosphoric acid-treated powder, etc.

One type of these hydrophobic powders may be used, or two or more types of the hydrophobic powders may be used. Further, the hydrophobic powder need only to be a hydrophobic powder which is applicable to ordinary cosmetics, and is not limited to the components exemplified above.

It is preferable for the content of the hydrophobic powder in the oil in water type solid cosmetic of the present disclosure to be preferably 0.1 to 40% by mass, more preferably 1 to 30% by mass, and still more preferably 5 to 25% by mass. If the content of the hydrophobic powder is excessively small, the cosmetic effect may decrease. Meanwhile, if the content is excessively great, there is a tendency for the cosmetic to become powdery and for stability to deteriorate.

<(D) Oil Component>

The oil component which is to be employed as component (d) in the oil in water type solid cosmetic of the present disclosure incorporates a hydrophobic powder or the like to constitute an inner layer (oil layer). There are no particular restrictions on the oil component as long as it is an oil component which is generally employed in cosmetics. Oils and fats, waxes, hydrocarbon oils, higher fatty acids, higher alcohols, synthetic ester oils, silicones, etc. may be employed. However, the oil component is not limited to these examples.

Examples of the oils and fats include, liquid oils such as avocado oil, camellia oil, evening primrose oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, eno oil, soybean oil, peanut oil, tea seed oil, kaya oil, rice bran oil, sunflower oil, Japanese tung oil, jojoba oil, germ oil, triglycerol, glycerol trioctanoate, triisopalmitic acid glycerin; and solid fats such as cacao butter, coconut oil, horse fat, hardened coconut oil, palm oil, beef fat, sheep fat, hardened beef fat, palm kernel oil, pork fat, beef bone fat, wolfberry kernel oil, hardened oil, beef leg fat, wolfberry, and hardened castor oil.

Examples of waxes include beeswax, candelilla wax, cotton wax, carnauba wax, bayberry wax, insect wax, spermaceti, montan wax, nucca wax, lanolin, kapok wax, lanolin acetate, liquid lanolin, sugarcane wax, isopropyl lanolin fatty acid, hexyl laurate, reduced lanolin, Burrow, hard lanolin, shellac wax, POE lanolin alcohol ether, POE lanolin alcohol acetate, POE cholesterol ether, lanolin fatty acid polyethylene glycol, POE hydrogenated lanolin alcohol ether, etc.

Examples of the hydrocarbon oils include oils such as liquid paraffin, ozokerite, squalene, pristane, paraffin, ceresin, squalene, petrolatum, microcrystalline wax, etc.

Examples of the higher fatty acids include lauric acid, myristic acid, palmitic acid, stearic acid, behenic acid, oleic acid, 12-hydroxystearic acid, undecylenic acid, tallic acid, isostearic acid, linoleic acid, linolenic acid, eicosapentaenoic acid (EPA), docosahexaenoic acid (DHA), etc.

Examples of higher alcohols include straight chain alcohols such as lauryl alcohol, cetyl alcohol, stearyl alcohol, behenyl alcohol, myristyl alcohol, oleyl alcohol, and cetostearyl alcohol; and branched chain alcohols such as monostearyl glycerin ether (batyl alcohol), 2-decyltetradecinol, lanolin alcohol, cholesterol, phytosterol, hexyldodecanol, isostearyl alcohol, octyldodecanol, etc.

Examples of the synthetic ester oils include isopropyl myristate, cetyl octanoate, octyldodecyl myristate, isopropyl palmitate, butyl stearate, hexyl laurate, myristyl myristate, decyl oleate, hexyldecyl dimethyl octanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprate, malic acid diisostearyl, glycerin di-2-heptylundecanoate, trimethylolpropane tri-2-ethylhexylate, trimethylolpropane triisostearate, tetra-2-ethylhexyl pentane erythritol, glyceryn tri-2-ethylhexylate, trimethylolpropane triisostearate, cetyl 2-ethylhexanoate, 2-ethylhexyl palmitate, trimyristic acid glycerin, tri-2-heptylundecanoic acid glyceride, castor oil fatty acid methyl ester, oleic acid oil, acetoglyceride, 2-heptylundecyl palmitate, diisobutyl adipate, N-lauroyl-L-glutamic acid 2-octylbutyldodecyl ester, adipic acid di-2-heptylundecil, ethyl laurate, sebacic acid di-2-ethylhexyl, di-2-hexyldecyl myristate, 2-hexyldecyl palmitate, 2-hexyldecyl adipate, sebacic acid diisopropyl, 2-ethylhexyl succinate, ethyl acetate, butyl acetate, amyl acetate, triethyl citrate, crotamiton ($C_{13}H_{17}NO$), etc.

Examples of the silicone include chain polysiloxanes such as dimethylpolysiloxane, methylphenylpolysiloxane, and methylhydrogenpolysiloxane; cyclic polysiloxanes such as decamethylcyclopentasiloxane, dodecamethylcyclohexasiloxane, tetramethyltetrahydrogenpolysiloxane; a silicone resin forming a three dimensional network structure; a silicone rubber; etc.

It is preferable for the content of the oil component in the solid cosmetic composition of the present disclosure to be 3 to 50% by mass, and more preferably 5 to 30% by mass. If the content of the oil component is less than 3% by mass, there are cases in which adhesion to skin is poor, and if the oil component is added in excess of 50% by mass, the cosmetic becomes likely to feel oily.

<(E) Water>

The content of water in the oil in water type solid cosmetic composition of the present disclosure is the balance of the content and is not limited as long as it can form the solid preparation of the present disclosure. The water content is generally within a range from 20 to 80% by mass, more and preferably within a range from 30 to 70% by mass. If the content of water is within this range, it will be possible to maintain a solid state more favorably, and it will be possible to prepare an oil in water type solid cosmetic composition that exhibits a superior sensation of freshness and spreading properties.

In addition to the above components, the oil in water type solid cosmetic of the present disclosure may contain a microgel which is obtained by crushing a gel formed by a hydrophilic compound having a gelling ability. By including such a microgel, a more favorable sensation of elasticity will be imparted, and it will become possible to further improve the ease with which the cosmetic composition can be taken up with an applicator, or a finger, etc.

In the present disclosure, a microgel having an average particle size within a range from 0.1 to 1000 μm, which is obtained by dissolving a hydrophilic compound having gelling properties in water or an aqueous component and then allowing to stand and cool to become a gel, and then crushed may be favorably employed. Such a microgel thickening agent differs from thickening polysaccharides or synthetic polymer thickening agents which are conventionally used in cosmetics in that the microgel thickener does not exhibit a thickening effect due to entanglement at a molecular level, but due to friction among the crushed gel microgel particles. Accordingly, threading properties which are characteristic to polymer solutions are not observed at all and a very refreshing feeling of use can be realized. In addition, polymer solutions undergo viscosity reduction due to the influence of formulations, salts, etc. which are blended thereinto, resulting in cases in which blends are limited. However, there is no such concern if the microgel is employed.

The hydrophilic compound having a gelling ability that forms the microgel is not particularly limited as long as it can be used in the field of cosmetics and pharmaceuticals. Specific examples thereof include hydrophilic proteins such as gelatin and collagen; as well as hydrophilic polysaccharides such as agar, curdlan, scleroglucan, schizophyllan, gellan gum, alginic acid, carrageenan, mannan, pectin, and hyaluronic acid. Among these, gelatin, agar, curdlan, gellan gum, alginic acid and carrageenan are particularly preferably used because they are not likely to be influenced by salts or ions, and are capable of preparing a stable gel. One type or two or more types of hydrophilic compounds having a gelling ability may be employed.

The method for preparing the microgel using the hydrophilic compound having a gelling ability is not particularly limited, and a common method can be used. For example, the microgel may be prepared according to the preparation method disclosed in Japanese Unexamined Patent Publication No. 2011-231061.

The content of such a microgel is not particularly limited, but is preferably within a range from 0.1 to 2.0% by mass, and more preferably within a range from 0.2 to 2.0% by mass, with respect to the total amount of the oil in water type solid cosmetic composition. Within such a range, a more preferable feeling of elasticity can be imparted, and it is possible to further improve the ease with which the cosmetic composition can be taken up with an applicator, or a finger, etc.

Various components which are generally employed in cosmetics, such as water soluble thickening agents other than those above, surfactants, humectants, ultraviolet ray absorbers, pH adjustors, antioxidants, antiseptics, antibacterial agents, pharmaceutical agents, plant extracts, fragrances, and pigment may be blended in the cosmetic composition of the present disclosure, within a range that does not adversely affect the effects thereof.

Examples of the water soluble thickening agents include cellulose derivatives such as carboxymethylcellulose, methylcellulose, hydroxymethylcellulose, hydroxyethylcellulose, and hydroxypropylcellulose, natural polymers such as sodium alginate, carrageenan, quince seed gum, xanthan gum, locust bean gum and pectin, as well as synthetic polymers such as polyvinyl alcohol, carboxyvinyl polymer, alkyl added carboxyvinyl polymer, sodium polyacrylate, sodium polymethacrylate, polyacrylic acid glycerin ester, and polyvinyl pyrrolidone. One type or two or more types of the water soluble thickening agents may be employed.

Examples of the surfactants include hydrophilic nonionic surfactants such as POE (10 to 50 mol) 2-octyldodecyl ether, POE (10 to 50 mol) decyltetradecyl ether, POE (10 to 30 mol) behenyl ether, POE (10 to 50 mol) cetyl ether, POE (20 to 60 mol) sorbitan monooleate, POE (10 to 60 mol) sorbitan monoisostearate, POE (10 to 50 mol) phytosterol ether, POE (20 to 100 mol) hardened castor oil derivative, POE (5 to 30 mol) POP (5 to 30 mol) 2-decyltetradecyl ether, POE (10 to 50 mol) POP (2 to 30 mol) cetyl ether, POE (10 to 80 mol) glyceryl monoisostearate, POE (10 to 30 mol) glyceryl monoisostearate, and polyether modified silicone; and hydrophilic anionic surfactants such as, for example, POE alkyl ether phosphate, POE•POP alkyl ether phosphate, POE sterol ether phosphate, POE•POP sterol ether phosphate, POE alkyl ether acetic acid, and POE•POP alkyl ether acetic acid. Among these, POE (30 mol) 2-octyldodecyl ether, POE (30 mol) phytosterol ether, POE (60 mol) hardened castor oil derivative, POE (30 mol) behenyl ether, POE (20 mol) glyceryl monoisostearate, POE (10 mol) methylpolysiloxane copolymer, etc. are preferable. Examples of commercially available surfactants include NIKKOL HCO-60, NIKKOL BPS-30, and NIKKOL BB-30 (by Nikko Chemicals Co., Ltd.); EMALEX GWIS-120 (by NIHON EMULSION Co., Ltd.); and KF-6017 (by Shin-Etsu Chemical industries), and the like.

Examples of the humectants include polyhydric alcohols such as glycerin, diethylene glycol, butylene glycol, polyethylene glycol, and dipropylene glycol; amino acids, nucleic acids, proteins such as collagen, and elastin; and mucopolysaccharides such as hyaluronic acid and chondroitin sulfate.

Examples of the ultraviolet ray absorbers include benzoic acid type ultraviolet ray absorbers such as paraaminobenzoic acid; anthranilic acid type ultraviolet ray absorbers such as methyl anthranilate; salicylic acid type ultraviolet ray absorbers such as octyl salicylate, phenyl salicylate, and homomethyl salicylate; cinnamic acid ultraviolet absorbers such as paramethoxy cinnamon acid isopropyl, octyl paramethoxycinnamate, 2-ethylhexyl paramethoxycinnamate, glyceryl diparamethoxycinnamate mono-2-ethylhexanoate, [4-bis (trimethylsiloxy) methylsilyl-3-methylbutyl]-3,4,5-trimethoxycinnamic acid ester; urocanic acid, ethyl urocaninate, 2-phenyl-5-methylbenzoxazole, 2-(2'-hydroxy-5'-methylphenyl) benzotriazole, 4-tert-butyl-4'-methoxy benzoyl methane, bis (resorushiniru) triazine, etc.

Examples of the pH adjustors include lactic acid, citric acid, sodium citrate, glycolic acid, succinic acid, tartaric acid, dl-malic acid, potassium carbonate, sodium bicarbonate, ammonium hydrogen carbonate, etc.

Examples of the antioxidants include ascorbic acid, α-tocopherol, dibutylhydroxytoluene, butylhydroxyanisole, etc.

Examples of the antiseptics and the antibacterial agents include paraoxybenzoic acid esters, phenoxyethanol, octoxyglycerin, benzoic acid, salicylic acid, carbolic acid, sorbic acid, parachlorometacresol, hexachlorophene, benzalkonium chloride, chlorhexidine chloride, trichlorocarbanilide, photosensitive elements, etc.

The oil in water type solid cosmetic of the present disclosure is not limited as long as it is in a solid form, and can be formed into an arbitrary shape such as in the form of a balm, in the shape of a stick, etc. Particularly in the case that the cosmetic composition is in the form of a balm, the sensation of elasticity and the ease with which the cosmetic composition can be taken up with a finger can be felt, and therefore is preferable.

In addition, the oil in water type solid cosmetic of the present disclosure is not limited, but preferably has a hardness of 100 or less, and more preferably has a hardness within a range from 15 to 75 from the viewpoint of usability. With a hardness in such a range, the ease with which the cosmetic composition can be taken up with a finger is improved further, and the cosmetic composition can also be stored in a stable manner.

Further, the oil in water type solid cosmetic of the present disclosure preferably has a stress ratio within a range from 0.8 to 1.0 as shown below. With a stress ratio within such a range, a more preferable sensation of elasticity can be felt:

Stress ratio=(stress value due to high speed penetration*[1])/(stress value due to low speed penetration*[2])

In addition, the oil in water type solid cosmetic of the present disclosure was measured with a texture analyzer manufactured by Stable Micro System Co., under the following conditions: a 5 mm φ needle, a penetration speed of 0.1 mm/sec, with a penetration distance of up to 0.5 mm. A ratio (B/A) of a stress/distance (B) up to 1.0 mm measured under the same conditions to a stress/distance (A) up to 0.5 mm is preferably within a range from 0.4 to less than 1, more preferably within a range from 0.5 to 0.8, and still more preferably within a range from 0.5 to 0.75.

*[1]: Measured using a texture analyzer by Stable Micro System, under the following conditions: a 5 mm φ needle, a penetration speed of 0.1 mm/sec, and a penetration value of 0.5 mm

*[2]: Measured using a texture analyzer manufactured by Stable Micro System, under the following conditions: a 5 mm φ needle, a penetration speed of 0.02 mm/sec, and a penetration value of 0.5 mm.

The form of preparation of the oil in water type solid cosmetic of the present disclosure is as a solid, and the product aspect thereof is not particularly limited, but examples include makeup cosmetics such as foundation, eye shadow, rouge, lipstick, etc., base cosmetics, skin care cosmetics, massage products, sun care products, body care products, etc. The advantageous effects of the present disclosure are significantly exhibited particularly in a makeup cosmetic.

The method for producing the oil in water type solid cosmetic preparation of the present disclosure is not particularly limited, and a conventional method may be employed. For example, it is possible to heat and mix components (e), (b) and a portion or the entirety of component (a) to prepare an aqueous phase portion. Meanwhile, components (d) and (c) may be heated and mixed to prepare an oil phase portion. Thereafter, the oil phase portion may be added to the aqueous phase portion and uniformly dispersed therein. If necessary, the remaining thickening components may be added, the mixture may be heated and mixed. Finally, the mixture may be poured into dish containers and the like, and then cooled to room temperature to become a solid.

EXAMPLES

Hereinafter, the present disclosure will be described in detail with reference to examples, but the present disclosure is not limited to the following examples. Note that unless otherwise specified, the content of each component is indicated as % by mass with respect to the system in which the component is blended.

Oil in water type solid cosmetic compositions were produced by a conventional method to be described below according to the formulations shown in Table 1, and the following evaluations were conducted. Note that in the examples, a (PEG-240/decyltetradeceth-20/HDI) copolymer (trade name "Adekanol GT-700" by ADEKA) was used as the hydrophobically modified polyether urethane of component (a).

[Production Method]
A. Heat and dissolve the aqueous phase components.
B. Add hydrophobic powder to the oil phase component, heat, and mix.
C. While stirring A, add and mix the hydrophilic powder and thickening components.
D. While stirring C, add B and mix uniformly while heating.
E. Fill a container with D and solidify by cooling to room temperature to obtain an oil in water solid eye shadow in the form of a balm.

[Evaluation Method]
<Stress Ratio>

Stress values were measured using a texture analyzer by Stable Micro System, at a high speed (0.1 mm/sec) and at a low speed (0.02 mm/sec) under the following conditions: a 5 mm φ needle and a penetration value of 0.5 mm. Stress ratios (stress value under a high speed condition/stress value under a low speed condition) were calculated at the point in time that the penetration distance of the needle was 0.5 mm.

<Hardness>

The hardness of each sample was measured as peak readings using a sun rheometer (CMPAC-II by Sun Science) under the following conditions: a 5.6 mm φ disc needle, a penetration distance of 2 mm, and a penetration speed of 20 mm/min.

<Sensation of Elasticity>

A panel of experts (10 women) was asked to touch each sample by hand. The sensation of elasticity for each sample was evaluated based on the criteria below.

(Evaluation Criteria)
Excellent: Eight or more members state that they feel a sensation of elasticity
Good: Five to seven members state that they feel a sensation of elasticity
Fair: Three to four members state that they feel a sensation of elasticity
Poor: Two or fewer members state that they feel a sensation of elasticity <Ease of Take Up with a Finger>

A panel of experts (10 women) was asked to take up and utilize each sample with a fingertip. The ease of take up with a finger for each sample was evaluated based on the criteria below.

(Evaluation Criteria)
Excellent: Eight or more members state that take up of the sample with a fingers is easy
Good: Five to seven members state that take up of the sample with a fingers is easy
Fair: Three to four members state that take up of the sample with a fingers is easy
Poor: Two or fewer members state that take up of the sample with a fingers is easy <Sensation of Freshness After Application>

A panel of experts (10 women) was asked to take up and utilize each sample with a fingertip. The sensation of freshness after application for each sample was evaluated based on the criteria below.
(Evaluation Criteria)
Excellent: Eight or more members state that they feel a sensation of elasticity Good: Five to seven members state that they feel a sensation of elasticity Fair: Three to four members state that they feel a sensation of elasticity Poor: Two or fewer members state that they feel a sensation of elasticity

TABLE 1

|  | Ingredient | Example 1 | Example 2 | Example 3 | Example 4 | Example 5 | Example 6 | Example 7 |
|---|---|---|---|---|---|---|---|---|
| Aqueous Phase | Water | Balance | Balance | Balance | Balance | Balance | Balance | Balance |
|  | Dipropylene Glycol | 9 | 9 | 9 | 9 | 9 | 9 | 9 |
|  | Gellan Gum(*1) | 0.75 | 0.75 | 0.75 | 0.75 | 0.75 | 0.75 | 0.75 |
|  | Antiseptic Agent | 0.5 | 0.5 | 0.5 | 0.5 | 0.5 | 0.5 | 0.5 |
|  | Polyoxyethylene Hardened Castor Oil (60) | 1.5 | 1.5 | 1.5 | 1.5 | 1.5 | 1.5 | 1.5 |
| Hydrophilic Powder | Plate Shaped Synthetic Mica (Aspect Ratio: 20)(*2) | 0.1 |  |  |  |  |  |  |
|  | Plate Shaped Synthetic Mica (Aspect Ratio: 40)(*3) |  | 0.1 |  |  |  |  |  |
|  | Plate Shaped Synthetic Mica (Aspect Ratio: 60)(*4) |  |  | 0.1 |  | 0.5 | 1 | 0.05 |
|  | Plate Shaped Synthetic Mica (Aspect Ratio: 100)(*5) |  |  |  | 0.1 |  |  |  |
|  | Spherical Silica Powder (Aspect Ratio: <10)(*6) |  |  |  |  |  |  |  |
|  | Spherical Porous Silica Powder (Particle Size: 3 to 5 μm) |  |  |  |  |  |  |  |
| Thickening Component | (PEG-240/Decyltetradeceth-20/HDI) Copolymer(*7) | 0.5 | 0.5 | 0.5 | 0.5 | 0.5 | 0.5 | 0.5 |
|  | Bentonite(*8) |  |  |  |  |  |  |  |
|  | (Acryloyl Dimethyl Taurine Ammonium/ Beheneth-25Methacrylate) Cross Polymer(*9) |  |  |  |  |  |  |  |
| Oil Phase | Dimethyl Silicone (2cs)(*10) | 20 | 20 | 20 | 20 | 20 | 20 | 20 |
|  | Isostearic Acid | 1 | 1 | 1 | 1 | 1 | 1 | 1 |
|  | Polyglyceryal-3 Bis Butyldimethicone(*11) | 1 | 1 | 1 | 1 | 1 | 1 | 1 |
| Hydrophobic Powder | Dimethicone Treated Red Iron Oxide Coated Mica Titanium(*12) | 8 | 8 | 8 | 8 | 8 | 8 | 8 |
|  | Dimethicone Treated Titanium Oxide/ Silica Multilayer Coated Mica Titanium(*13) | 3 | 3 | 3 | 3 | 3 | 3 | 3 |
|  | Dimethicone Treated Iron Oxide Coated Mica Titanium(*14) | 9 | 9 | 9 | 9 | 9 | 9 | 9 |
|  | Total | 100 | 100 | 100 | 100 | 100 | 100 | 100 |
| Evaluations |  |  |  |  |  |  |  |  |
|  | Hardness | 41 | 40 | 40 | 43 | 43 | 45 | 40 |
|  | Sensation of Elasticity (Springiness) | Excellent | Excellent | Excellent | Excellent | Excellent | Good | Excellent |
|  | Take Up Properties with a Finger | Good | Excellent | Excellent | Excellent | Excellent | Excellent | Good |
|  | Sensation of Freshness after Application | Good | Good | Excellent | Excellent | Excellent | Good | Excellent |
|  | Remarks |  |  |  |  |  |  |  |

|  | Ingredient | Comparative Example 1 | Comparative Example 2 | Comparative Example 3 | Comparative Example 4 | Comparative Example 5 | Comparative Example 6 |
|---|---|---|---|---|---|---|---|
| Aqueous Phase | Water | Balance | Balance | Balance | Balance | Balance | Balance |
|  | Dipropylene Glycol | 9 | 9 | 9 | 9 | 9 | 9 |
|  | Gellan Gum(*1) | 0.75 | 0.75 | 0.75 | 0.75 | 0.75 | 0.75 |
|  | Antiseptic Agent | 0.5 | 0.5 | 0.5 | 0.5 | 0.5 | 0.5 |
|  | Polyoxyethylene Hardened Castor Oil (60) | 1.5 | 1.5 | 1.5 | 1.5 | 1.5 | 1.5 |
| Hydrophilic Powder | Plate Shaped Synthetic Mica (Aspect Ratio: 20)(*2) |  |  |  |  | 0.1 | 0.1 |
|  | Plate Shaped Synthetic Mica (Aspect Ratio: 40)(*3) |  |  |  |  |  |  |
|  | Plate Shaped Synthetic Mica (Aspect Ratio: 60)(*4) |  |  |  |  |  |  |
|  | Plate Shaped Synthetic Mica (Aspect Ratio: 100)(*5) |  |  |  |  |  |  |
|  | Spherical Silica Powder (Aspect Ratio: <10)(*6) |  | 0.1 | 0.2 |  |  |  |
|  | Spherical Porous Silica Powder (Particle Size: 3 to 5 μm) |  |  |  | 0.2 |  |  |
| Thickening Component | (PEG-240/Decyltetradeceth-20/HDI) Copolymer(*7) | 0.5 | 0.5 | 0.5 | 0.5 |  |  |
|  | Bentonite(*8) |  |  |  |  | 0.5 |  |
|  | (Acryloyl Dimethyl Taurine Ammonium/ Beheneth-25Methacrylate) Cross Polymer(*9) |  |  |  |  |  | 0.5 |
| Oil Phase | Dimethyl Silicone (2cs)(*10) | 20 | 20 | 20 | 20 | 20 | 20 |
|  | Isostearic Acid | 1 | 1 | 1 | 1 | 1 | 1 |
|  | Polyglyceryal-3 Bis Butyldimethicone(*11) | 1 | 1 | 1 | 1 | 1 | 1 |
| Hydrophobic Powder | Dimethicone Treated Red Iron Oxide Coated Mica Titanium(*12) | 8 | 8 | 8 | 8 | 8 | 8 |
|  | Dimethicone Treated Titanium Oxide/ | 3 | 3 | 3 | 3 | 3 | 3 |

TABLE 1-continued

| | | | | | | |
|---|---|---|---|---|---|---|
| Silica Multilayer Coated Mica Titanium(*13) Dimethicone Treated Iron Oxide Coated Mica Titanium(*14) | 9 | 9 | 9 | 9 | 9 | 9 |
| Total | 100 | 100 | 100 | 100 | 100 | 100 |
| Evaluations | | | | | | |
| Hardness | 38 | 50 | 63 | 42 | | |
| Sensation of Elasticity (Springiness) | Excellent | Fair | Poor | Fair | Poor | Poor |
| Take Up Properties with a Finger | Poor | Fair | Poor | Fair | Fair | Fair |
| Sensation of Freshness after Application | Excellent | Fair | Poor | Fair | Poor | Poor |
| Remarks | Water Separation | | | | | |

(*1)Kelco Gel Gellan Gum (by CP Kelco)
(*2)Mica ST (HS) (by Topy Industries)
(*3)Mica PDM-5L (by Topy Industries)
(*4)Mica PDM-9L (by Topy Industries)
(*5)Helios R100S (by Topy Industries)
(*6)Acrosil 380S (by Acrosil)
(*7)Adekanol GT-700 (by Adeka)
(*8)Kunipia G-5 (by Kuniminc Industries)
(*9)Aristoflex HMB (by Clariant Japan)
(*10)KF-96L-2cs (by Shinetsu Chemical Industries)
(*11)KF-6109 (by Shinetsu Chemical Industries)
(*12)SA-Gem Tone Tan Opal (by Miyoshi Kasei)
(*13)SA-Timiron Splendid Gold (by Miyoshi Kasei)
(*14)SA-Timiron-MP115 (by Miyoshi Kasei)

As shown in Table 1, Comparative Example 1, which does not contain any hydrophilic powder exhibited poor stability by releasing water. Comparative Examples 2 to 4, which contain spherical hydrophilic powder, exhibited poor take up properties with a finger. Further, none of the Comparative Examples exhibited a sensation of elasticity. On the other hand, by adding a plate shaped hydrophilic powder, oil in water type solid cosmetic compositions (Examples 1 through 7) in which water separation is prevented, that exhibits a desired sensation of elasticity, has favorable take up properties with a finger, and further imparts a sensation of freshness after application were obtained. In particular, Examples 2 through 4, in which hydrophilic plate shaped powders having aspect ratios of 40 or greater were blended, exhibited better take up properties with a finger and a further favorable sensation of freshness than Example 1, in which a hydrophilic plate shaped powder having an aspect ratio of less than 40 was blended. Comparative Examples 5 and 6, in which thickening agents different from the hydrophobically modified polyether urethane represented by Formula (I) were used, were not able to impart a desired sensation of elasticity or a sensation of freshness after application. Note that although data are not shown, the oil in water type solid cosmetic compositions of Examples 1 to 7 all have stress ratios within a range from 0.8 to 1.0 (stress value under a high speed condition/stress value under a low speed condition).

Next, in order to evaluate the physical properties that result in the unique sensation of elasticity of the solid cosmetic of the present disclosure, a texture analyzer by Stable Micro System was employed to measure a response profile of stress with respect to a penetration distance of up to 1 mm using a 5 mm φ needle at a penetration speed of 0.1 mm/sec. The results of measurement were compared to the response profiles of conventional solid type preparations and cream type preparation.

<Evaluation Samples>
Solid Sample A: oil in water type solid sample that employs wax
Solid Sample B: aqueous solid sample that employs agar-gellan gum
Solid Sample C: Product of the Present Disclosure (Example 4)
Liquid (Cream) Sample: Oil in Water Type Cream Sample The above samples were prepared by a conventional method according to the following formulations. The content of each component is indicated as % by mass with respect to the total amount of the cosmetic.

Formulation of Solid Sample A:
Oil in Water type Solid Cosmetic Composition
(1) decamethyl cyclopentasiloxane: 15.8
(2) candelilla wax: 2.0
(3) stearic acid: 1.0
(4) red iron oxide: 1.0
(5) yellow iron oxide: 3.0
(6) black iron oxide: 0.2
(7) titanium dioxide: 10.0
(8) kaolin: 5.0
(9) talc: 25.8
(10) 1,3-butylene glycol: 3.0
(11) methylparaben: 0.2
(12) ion exchange water: balance
(13) 2-alkyl-N-carboxymethyl-N-hydroxyethylimidazolinium betaine (pure content 30%): 5.0

Formulation of Solid Sample B:
Aqueous Solid Cosmetic Composition
(1) agar: 1.0
(2) gellan gum: 0.5
(3) table salt: 0.5
(4) DPG: q. s.
(5) dye: q. s.
(6) ion exchange water: balance Formulation of Solid Sample C (Product of the Present Disclosure):
Oil in Water Type Solid Cosmetic Composition
The same formulation as that of Example 4 above was employed.

Formulation of Liquid (Cream) Sample:
Oil in Water Type Cosmetic Composition
(1) Carbomer: 0.3
(2) acrylic acid/alkyl acrylate (C10-30): 0.3 Copolymer
(3) dimethicone: 3.0

(4) glycerin: q. s.

(5) DPG: q. s.

(6) ion exchange water: balance

Figure 1A:
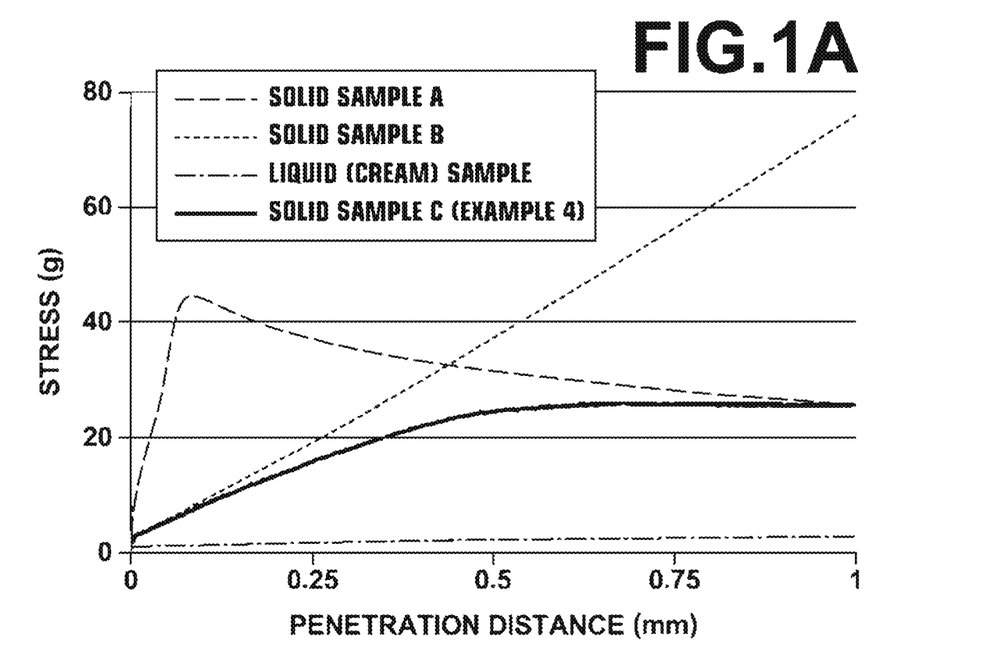
FIG. 1A is a graph that illustrates the relationship between penetration distance and applied force for each sample: solid sample A (--); solid sample B (----); liquid (cream) sample (----); and solid sample C (Example 4) (-).
Figure 1B:
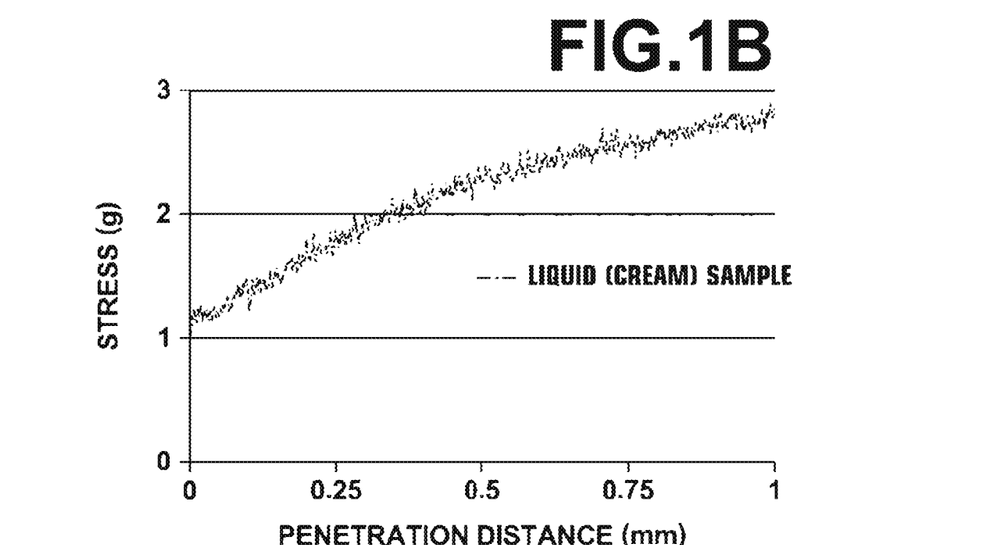
FIG. 1B is a graph showing an enlarged scale of the vertical axis of the liquid (cream) sample illustrated in FIG. 1A.

The results are shown in FIG. 1A. Solid Sample A was a solid sample that employs wax, and exhibited a stress that proportionally increased with respect to the penetration distance immediately after penetration. The stress increased substantially linearly, but the structure was destroyed at a certain point (yield value), after which the stress gradually decreased. Solid Sample B was an aqueous solid sample that employs agar-gellan gum. However, because the stress increased proportionally with respect to the penetration distance and the graph is linear within the measurement range and under the conditions which were employed, it can be understood that Solid Sample B exhibits the behavior of a general elastic body. Meanwhile, in Solid Sample C (Example 4) as the product of the present disclosure, the change in stress with respect to the penetration distance was curved. This is due to a viscous factor and is generally a behavior which is observed in viscoelastic bodies such as a liquid form (cream form). Actually, FIG. 1B illustrates a graph of the liquid form (cream form) sample of FIG. 1A, in which the vertical axis is magnified. The shape of the graph of Solid Sample C is similar to the shape of the graph of the liquid form (cream form) sample. Despite being in a solid form (the form of a balm), the present disclosure exhibits viscoelastic behavior similar to that of a cream, which is thought to result in a unique tactile sensation that imparts a feeling of elasticity.

Figure 2:
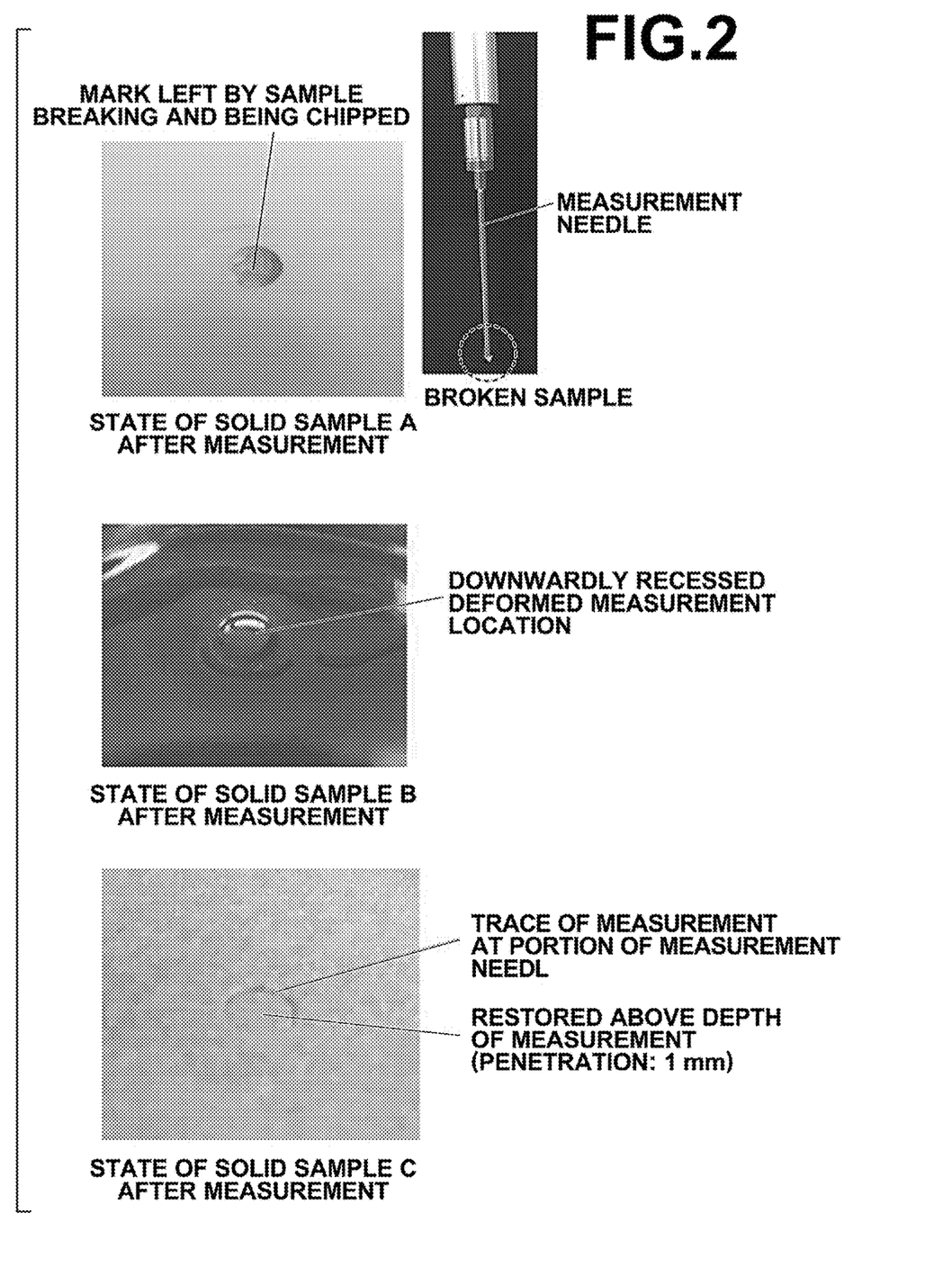
FIG. 2 is a photograph of the measurement surface of each sample after measuring the relationship between penetration distance and applied force: top (solid sample A); middle (solid sample B); bottom (solid sample C).

Further, as described above, the samples were recovered after measuring the relationship between the penetration distance and stress, and the measurement surfaces thereof were observed. FIG. 2 is a collection of photographs of the measurement surfaces of each sample (Solid Samples A, B and C). In Solid Sample A, the measurement location was broken, and the measurement location was deformed in Solid Sample B. In contrast, in Solid Sample C (Example 4), which is the product of the present disclosure, although a measurement trace remained, restorability was confirmed, and the unique sensation of elasticity of the solid cosmetic composition of the present disclosure was confirmed here as well.

Figure 3:
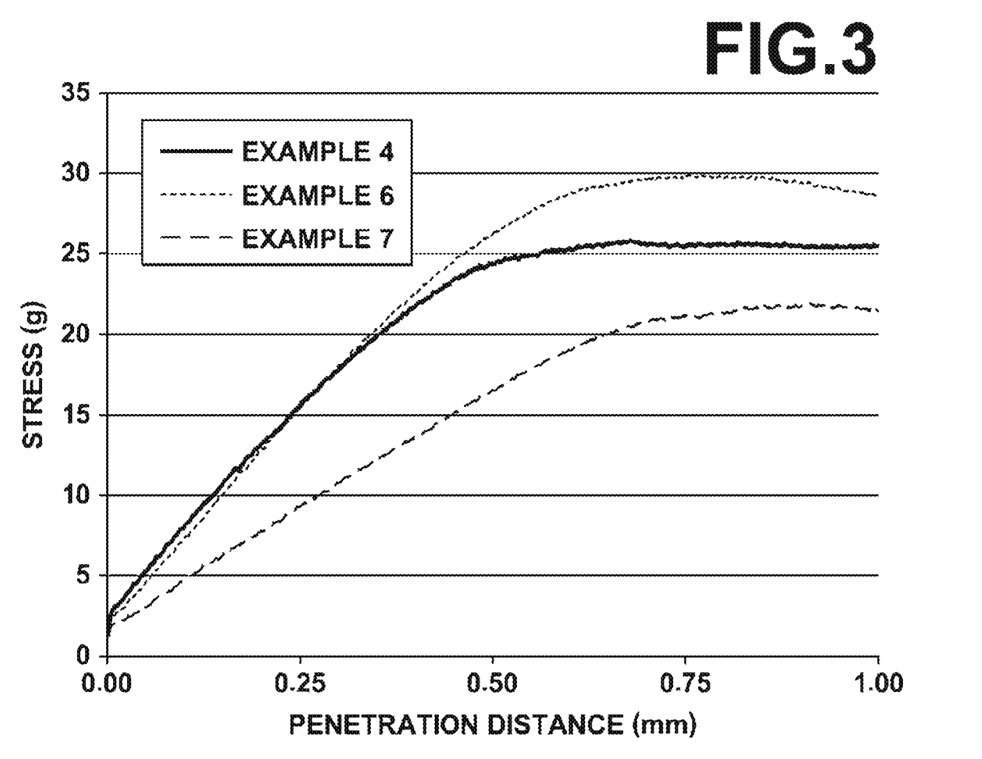
FIG. 3 is a graph showing the relationship between penetration distance and applied force for three types of products of the present disclosure having different degrees of hardness: Example 4 (-); Example 6 (----); and Example 7 (--).

Next, the physical properties of the solid cosmetic of the present disclosure were further evaluated using a texture analyzer by Stable Micro System. Response profiles of stress with respect to a penetration distance of up to 1 mm using a 5 mm needle at a penetration speed of 0.1 mm/sec were measured for samples of Example 6 (hard/a hardness of 45) and Example 7 (soft/a hardness of 40), each of which have a different hardness from that of Solid Sample C, in addition to Solid Sample C (Example 4/a hardness of 43) employed as described above. As illustrated in FIG. 3, in the samples of Examples 6 and 7 as well, the stress behavior with respect to the penetration distance shows a gentle upwardly convex curve, which indicates viscoelastic behavior as in Solid Sample C (Example 4). A ratio (B/A) of the stress/distance (B) at a penetration distance of up to 1.0 mm with respect to the stress/distance (A) at a penetration distance of up to 0.5 mm was calculated for each sample, and is shown in Table 2 below. Note that the same ratios were similarly calculated for Solid Sample A and the liquid form (cream) sample which were employed above, as comparative samples.

TABLE 2

| | Comparative Samples | | Samples of the Present Invention | | |
|---|---|---|---|---|---|
| | Solid Sample A | Liquid (Cream) Sample | Solid Sample C (Example 4) | Example 6 | Example 7 |
| Penetration Distance (mm) | | | Stress (g) | | |
| 0 | 1.85 | 1.15 | 1.75 | 1.47 | 1.61 |
| 0.5 | 37.40 | 2.29 | 24.36 | 26.24 | 16.59 |
| 1 | 76.10 | 2.78 | 24.45 | 28.58 | 21.43 |
| A: Stress/Distance up to 0.5 mm | 71.1 | 2.28 | 45.22 | 49.54 | 29.96 |
| B: Stress/Distance up to 1.0 mm | 74.25 | 1.63 | 22.7 | 27.11 | 19.82 |
| B/A | 1.04 | 0.71 | 0.50 | 0.55 | 0.66 |

Solid sample A, which exhibited behavior close to that of an elastic body in the range up to 1 mm had a B/A value close to 1, whereas the liquid form (cream) sample, which exhibited viscoelastic behavior had a B/A value of less than 1. Each of the products of the present disclosure had a B/A value of less than 1 similarly to the cream, although being in a solid state (having no fluidity).

Hereinafter, examples of formulations of the oil in water type solid cosmetic composition of the present disclosure will be described as examples. The content of each component is indicated as % by mass with respect to the total amount of the cosmetic, and the cosmetics are prepared in the same manner as described above.

Formulation Example 1: Eyeshadow dipropylene glycol: 7
gellan gum: 0.9
glycerin: 2
carboxymethyl cellulose: 0.15
phenoxy ethanol: 0.5
polyoxyethylene hardened castor oil: 1.5
plate shaped synthetic mica (*2): 0.1
(PEG-240/decyltetradeceth-20/HDI): 0.6
Copolymer (*7)
dimethylsilicone (2 cs): 20
isostearic acid: 1
polyglyceryl-3 bis butyldimethicone: 1
silicone treated red iron oxide coated mica titanium: 10
silicone treated red iron oxide coated mica: 10
water: balance
Total: 100

Formulation Example 2: Eyeshadow dipropylene glycol: 9
gellan gum 0.75
carboxymethyl cellulose: 0.15
phenoxy ethanol: 0.5
polyoxyethylene hardened castor oil: 1.5
plate shaped synthetic mica (*3): 0.1
(PEG-240/decyltetradeceth-20/HDI): 0.6
Copolymer (*7)
dimethylsilicone (2 cs): 20
isostearic acid: 1
polyglyceryl-3 bis butyldimethicone: 1
silicone treated red iron oxide coated mica titanium: 7.8
silicone treated titanium oxide/silica multilayer coated mica titanium: 3.2 water: balance
Total: 100

Formulation Example 3: Eyeshadow dipropylene glycol: 9
tamarind seed gum 0.5
carboxymethyl cellulose 0.15
phenoxy ethanol 0.5
polyoxyethylene hardened castor oil 1.5
plate shaped synthetic mica (*3): 0.1
(PEG-240/decyltetradeceth-20/HDI): 0.6
    Copolymer (*7)
dimethyl silicone (2 cs): 20
isostearic acid: 1
PEG-9 polydimethylsiloxyethyl dimethicone: 0.3
methyl polysiloxane-treated mica titanium: 20
water: balance
Total: 100

Formulation Example 4: Foundation 1,3 butylene glycol: 9
gellan gum: 0.45
agar: 0.15
glycerin: 1
carboxymethyl cellulose: 0.15
phenoxy ethanol 0.5
polyoxyethylene hardened castor oil: 1.5
plate shaped synthetic mica (*4): 0.1
(PEG-240/decyltetradeceth-20/HDI): 0.6
    Copolymer (*7)
dimethylsilicone (2 cs): 20
sorbitan isostearate: 1
polyglyceryl-3 bis butyldimethicone: 1
hydrophobized fine titanium oxide particles: 5
hydrophobized pigment grade titanium oxide: 1
hydrophobized yellow iron oxide: 0.2
hydrophobized yellow iron oxide: 0.05
hydrophobized black iron oxide: 0.01
water: balance
Total; 100

Formulation Example 5: Base Makeup propylene glycol: 8
gellan gum: 0.7
carboxymethyl cellulose: 0.15
phenoxy ethanol: 0.5
polyoxyethylene hardened castor oil: 1
polyoxyethylene behenyl ether: 0.5
plate shaped synthetic mica (*5): 0.1
(PEG-240/decyltetradeceth-20/HDI): 0.5
    Copolymer (*7)
dimethyl silicone (1.5 cs): 20
sorbitan isostearate: 1
polyglyceryl-3 bis butyldimethicone: 1
(diphenyl dimethicone/vinyl diphenyl dimethicone/silsesquioxane) cross polymer: 6
hydrophobized fine titanium oxide particles: 5
hydrophobized pigment grade titanium oxide: 2
hydrophobized yellow iron oxide: 0.4
hydrophobized yellow iron oxide: 0.12
hydrophobized black iron oxide: 0.02
hydrophobized mica: q. s.
water: balance
Total: 100

Formulation Example 6: Skin Care Balm propylene glycol: 8
gellan gum: 1
carboxymethyl cellulose: 0.15
phenoxy ethanol: 0.5
polyoxyethylene glyceryl isostearate: 1.5
plate shaped synthetic mica (*4): 0.1
(PEG-240/decyltetradeceth-20/HDI): 0.8
    Copolymer (*7)
dimethyl silicone (2 cs): 12
dimethyl silicone (6 cs): 8
sorbitan isostearate: 1
polyglyceryl-3 bis butyldimethicone: 1
(diphenyl dimethicone/vinyl diphenyl dimethicone/silsesquioxane) cross polymer: 6
hydrophobized mica: 10
water: balance
Total: 100

Each of the oil in water type solid cosmetic compositions of the above Formulation Examples imparted a sensation of elasticity when touched, had favorable take up properties with a finger, and exhibited superior spreading properties as well as a superior sensation of freshness during application.

The invention claimed is:
1. An oil in water solid cosmetic, comprising:
   (a) 0.1 to 5% by mass of a hydrophobically modified polyether urethane represented by Formula (I) below;
   (b) 0.01 to 5% by mass of a hydrophilic plate shaped powder;
   (c) 5 to 25% by mass of a hydrophobic powder;
   (d) an oil component;
   (e) water; and
   (f) 0.1 to 2.0% by mass of a gellan gum;

$$R_1-\{(O-R_2)_k-OCONH-R_3[-NHCOO-(R_4-O)_n-R_5]_h\}_m \quad \text{Formula (I):}$$

wherein:
   $R_1$, $R_2$ and $R_4$ each independently represent a hydrocarbon group having 2 to 4 carbon atoms;
   $R_3$ represents a hydrocarbon group having 1 to 10 carbon atoms which may have a urethane bond;
   $R_5$ is a hydrocarbon group having 8 to 36 carbon atoms;
   m is a number 2 or greater;
   h is a number 1 or greater;
   k is a number within a range from 1 to 500;
   n is a number within a range from 1 to 200,
   the average aspect ratio of the (b) hydrophilic plate shaped powder is within a range from 10 to 100, and
   a ratio B/A of a stress/distance (B) to a stress/distance (A) measured with a texture analyzer manufactured by Stable Micro System Co., under the following conditions is 0.50 to 0.66:
   a stress/distance (A) is measured under the condition of 5 mm φ needle, a penetration speed of 0.1 mm/sec, with a penetration distance up to 0.5 mm, and
   a stress/distance (B) is measured under the condition: 5 mm φ needle, a penetration speed of 0.1 mm/sec, with a penetration distance up to 1.0 mm.

2. The oil in water solid cosmetic as defined in claim 1, wherein:
   the (a) hydrophobically modified polyether urethane is a (PEG-240/decyltetradeceth-20/HDI) copolymer.

3. The oil in water solid cosmetic as defined in claim 1, wherein:

the oil in water solid cosmetic is in the form of a balm.

4. The oil in water solid cosmetic as defined in claim 1, wherein:

the oil in water solid cosmetic is a makeup cosmetic.

5. The oil in water solid cosmetic as defined in claim 2, wherein:

the oil in water solid cosmetic is in the form of a balm.

6. The oil in water solid cosmetic as defined in claim 2, wherein:

the oil in water solid cosmetic is a makeup cosmetic.

7. The oil in water solid cosmetic as defined in claim 3, wherein:

the oil in water solid cosmetic is a makeup cosmetic.

* * * * *